United States Patent
Zhang (12)

(10) Patent No.: US 6,527,728 B2
(45) Date of Patent: Mar. 4, 2003

(54) PROCESS AND DEVICE FOR DETERMINING THE PULSE TRANSIT TIME AND EXTRACORPOREAL HEMOTHERAPEUTIC ARRANGEMENT WITH SUCH A DEVICE

(75) Inventor: Wei Zhang, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/982,238

(22) Filed: Oct. 19, 2001

(65) Prior Publication Data

US 2002/0055672 A1 May 9, 2002

(30) Foreign Application Priority Data

Oct. 19, 2000 (DE) .......................... 100 51 943

(51) Int. Cl.[7] .............. A61B 5/02; A61B 5/00
(52) U.S. Cl. ............ 600/500; 600/368; 600/481
(58) Field of Search .............. 600/500, 310, 600/368, 476, 479, 480, 481, 485, 504

(56) References Cited

U.S. PATENT DOCUMENTS

| | | | | |
|---|---|---|---|---|
| 4,807,638 A | * | 2/1989 | Sramek | 600/485 |
| 5,237,997 A | | 8/1993 | Greubel et al. | 128/672 |
| 5,830,131 A | * | 11/1998 | Caro et al. | 600/300 |
| 6,280,390 B1 | * | 8/2001 | Akselrod et al. | 600/485 |

FOREIGN PATENT DOCUMENTS

| | | |
|---|---|---|
| DE | 38 07 672 | 9/1989 |
| DE | 44 27 991 | 2/1996 |
| DE | 198 29 544 | 1/2000 |
| EP | 0 358 873 | 3/1990 |
| EP | 0 911 044 | 4/1999 |
| WO | 89/08424 | 9/1989 |
| WO | 94/23643 | 10/1994 |
| WO | 94/27495 | 12/1994 |
| WO | 98/51211 | 11/1998 |
| WO | 00/33053 | 6/2000 |

OTHER PUBLICATIONS

WPI/Derwent; AN 1989–218899; SU 1 435 239; Nov. 7, 1988.
Patent Abstracts of Japan; JP 11 089801; Apr. 6, 1999.
Fung; Biomechanics Circulation; 2nd edition; Springer, New York, Berlin, 1997, p. 140.
Gribbin et al.; Pulse Wave Velocity as a Measure of Blood Pressure Change; Psychophysiology, vol. 13, 86 (1976).

* cited by examiner

*Primary Examiner*—Max F. Hindenburg
*Assistant Examiner*—Navin Natnithithadha
(74) *Attorney, Agent, or Firm*—Jacobson Holman PLLC

(57) ABSTRACT

A process and a device for improving the determination of the pulse transit time for non-invasive blood pressure measurement. A value, correlating with the blood density, is determined and its influence on the pulse transit time is compensated. In this manner more precise blood pressure data can be obtained. In a further development, a value, correlating with the blood density, is determined by a measuring device for the change in relative blood volume or hematocrit. The device can also be used as part of a hemotherapeutic arrangement such as a hemodialysis device and/or hemofiltration device, in which a blood pressure monitoring as continuous and precise as possible is desired, among other things, because of a blood volume change and thereby a blood density change inherent in the therapy.

30 Claims, 2 Drawing Sheets

PROCESS AND DEVICE FOR DETERMINING THE PULSE TRANSIT TIME AND EXTRACORPOREAL HEMOTHERAPEUTIC ARRANGEMENT WITH SUCH A DEVICE

BACKGROUND

1. Field of the Invention

The invention relates to the field of determining the pulse transit time of a patient or donor where a pulse transit time is measured for pulse waves propagating via the patient's or donor's vascular system and created by his/her heart contractions.

2. Description of the Related Art

A patient's or donor's blood pressure is typically measured by means of an inflatable rubber cuff according to the Riva-Rocci method. This method allows a measurement only at a defined time, at which the pressure of the cuff is varied over a certain period of time. Thus, continuous measurement is limited to time intervals that are determined by the measuring method. A quasi continuous measurement would be associated with a constantly alternating expansion and deflation of the rubber cuff, which would be accompanied by unreasonable stress on the patient.

As an alternative to the non-invasive Riva-Rocci method, there exists a method for determining the pulse transit time, which can also be carried out non-invasively. This method is based on the knowledge that the time that a pulse wave, produced by a heart contraction of a patient or donor, requires to make its way through the vascular system from a first point to a second place is a function of the blood pressure of the person examined. If the time is measured that passes between the occurrence of a heartbeat (detected, for example, by means of an electrocardiograph (EKG)) and the time of arrival of the related pulse wave at an area of the body at a distance from the heart (detected, for example, by an optical sensor on the ear lobe or finger), this pulse transit time represents a direct measure of the patient's or donor's blood pressure. Since the pulse transit time varies from person to person, a calibration by means of an initial Riva-Rocci measurement is necessary. However, a statement on relative changes can be obtained directly from the relative changes in the pulse transit time. The relation between the blood pressure and the pulse transit time is largely linear (Psychophysiology, Vol. 3,86 (1976)). Since one measurement is possible per heart beat, this measuring method represents a semi-continuous blood pressure measurement.

The WO 89/08424 describes a measurement process for determining the pulse transit time by means of an electrocardiograph EKG and an optoelectronic measuring sensor on skin areas with good circulation. However, since the circulation in the skin tissue and thus also the photoelectric profile itself can change over time due to vasomotoric and other adjustments without the blood pressure necessarily having changed, a repeated recalibration should follow the initial calibration according to the Riva-Rocci method, using the measured values of the optoelectronic measuring sensor. In this respect, a constant relationship between the pulse transit time and the blood pressure is assumed for each person. The recalibration serves the purpose of allowing absolute statements about the systolic as well as the diastolic pressure from the photoelectric profiles at later points in time.

Acute emergencies, e.g. during hemodialysis and/or hemofiltration, require careful action. A primary complication during such a hemotherapy is a decrease in blood pressure. The most frequent cause of such an incident is a hypovolemia as a result of an excessively intensive fluid withdrawal. In particular during extracorporeal hemotherapy, it is, therefore, necessary to constantly monitor the blood pressure of a patient or donor in order to recognize possible circulation complications at an early stage.

The EP-A 0 911 044, which is hereby incorporated by reference, describes, among other things, a hemodialysis and/or hemofiltration apparatus, in which a continuous blood pressure monitoring with only a slight negative effect on the patient is made possible by means of a pulse transit time measurement. Using the measurement signal of the pulse transit time, it is possible to recognize critical blood pressure conditions at an early stage and to then inform the staff without delay. If necessary, countermeasures can be carried out automatically on the hemodialysis and/or hemofiltration apparatus, e.g. by infusions or modifying concentrations. This prior art apparatus, like the teaching of the WO 89/08424, assumes a constant relationship between the blood pressure and the pulse transit time. This assumption is not sufficiently accurate in the case of hemotherapies that It change the blood density in particular. In particular due to fluid withdrawal during a hemodialysis and/or hemofiltration treatment, the blood density increases during the course of the treatment (blood density in this case refers to the density of blood as a fluid per se). Since blood density has a direct influence on the pulse wave velocity and thus the pulse transit time, the results are inaccurate measurement values.

SUMMARY OF THE INVENTION

The present invention is based on the technical problem of improving a process and/or a device for determining a patient's or donor's pulse transit time in such a manner that the changes in the blood count are taken into account during the course of time and thus a more precise monitoring of blood pressure is made possible.

According to the teaching of the invention, this problem is solved by means of a process for determining the pulse transit time where a pulse transmit time is measured for pulse waves propagating via the patient's or donor's vascular system and created by his/her heart contractions, in which a value, correlating with the blood density, is determined and then used to calculate from the measured pulse transit time a pulse transit time, for which the influence of blood density is compensated.

The problem is also solved by a device for determining the pulse transit time with means for determining the pulse transit time of pulse waves, which are propagated via the patient's or donor's vascular system and are created by heart contractions, according to which there are means for determining a value, correlating with the blood density, and an evaluation unit that compensates for the influence of blood density on the pulse transit time.

The invention builds on the knowledge that the influence of a variable blood density between the two measurements can be compensated by means of measurements of a value, correlating with the blood density, at the time of a first pulse transit time measurement and at the time of a second pulse transit time measurement. In this manner a compensated first or second pulse transit time can be obtained that is directly comparable with the second or the first pulse transit time, as if it had been measured with constant blood density. In this manner, emergency conditions can be indicated with significantly greater reliability.

The rate at which a disturbance along an elastic, cylindrical, sufficiently long tube spreads in a homogenous fluid, may be expressed (Y. C. Fung, in "Biomechanics Circulation", 2nd edition, Springer, N.Y., Berlin, 1997, p. 140):

$$c=\sqrt{[(A/\rho)(dp/dA)]} \quad (1)$$

where
$\rho$: density of the fluid
A: cross section of the tube
dA: change in cross section
dp: change in pressure in the tube If equation (1) is assumed to be valid for blood in arteries, this results in equation (2) for blood with a density $\rho(t0)$ at time t0 compared to blood with a density of $\rho(t)$ at time t at constant blood pressure p(t0) for the pulse wave velocity c:

$$[c(t, p(t0), \rho(t))]/[c(t0, p(t0), \rho(t0))]=\sqrt{[\rho(t0)/\rho(t)]} \quad (2)$$

For the pulse transit time PTT, which indicates the passage of the pulse waves at the pulse wave propagation velocity over a defined path L, a similar expression is obtained:

$$PTT(t, p(t0), \rho(t))/PTT(t0, p(t0), \rho(t0))=L/c(t, p(t0), \rho(t))/L/c(t0, p(t0), \rho(t0))=\sqrt{[\rho(t)/\rho(t0)]} \quad (3)$$

By means of equation (3), it is possible to take into account the change in pulse transit time due to a change in blood density. For example, if at a time t0 a first pulse transit time PTT (t0,p(t0),$\rho$(t0)) was measured and at a second time t a second pulse transit time PTT (t,p(t),$\rho$(t)) was measured using equation (3), the influence of the different blood densities can be compensated. Each of the two pulse transit times can be converted to the blood density of the other measurement and thus made comparable:

$$PTT(t, p(t), \rho(t0))=PTT(t, p(t), \rho(t))\sqrt{[\rho(t0)/\rho(t)]} \quad (3a)$$

$$PTT(t0, p(t0), \rho(t))=PTT(t0, p(t0), \rho(t0))\sqrt{[\rho(t)/\rho(t0)]} \quad (3b)$$

The PTT data, compensated for the influence of blood density, can be directly compared and evaluated. If a calibration was carried out beforehand with an absolute blood measuring apparatus, the pulse transit time should be converted to the blood density at the time of the calibration measurements.

Thus, it continues to be possible to make a precise conversion into absolute blood pressure values.

The inventive process and/or the inventive device of the present invention embrace(s) this finding. In this respect it is sufficient to determine a value, correlating with the blood density, as long as the square roots in equations (3a) or (3b) can be determined for blood density compensation. The evaluation unit of the inventive device, which compensates for the influence of blood density on the pulse transit time, is suitable for carrying out a compensation, according to equations (3a) or (3b).

An especially preferred embodiment of the process, according to the invention, is used in an embodiment of the device, according to the invention, whereby the means for determining a value, correlating with the blood density, comprise a measuring device for determining the relative blood volume or the relative change in blood volume. Assuming that the change in density according to equation (3) was caused only by volumetric changes, but not by measurement changes, the following results for the root term from equation (3) with volumes V(t0) and V(t):

$$\sqrt{[\rho(t)/\rho(t0)]}=\sqrt{[m/V(t)/m/V(t0)]}=\sqrt{[V(t0)/V(t)]}=\sqrt{[V(t0)/V0/V(t)/V0]}=\sqrt{[RBV(t0)/RBV(t)]} \quad (4)$$

where V0 is a comparative volume for the relative blood volumes RBV. Thus, according to equation (4), it is sufficient to determine the relative change in blood volume; additional measurements for blood density or absolute data on blood volumes are not necessary.

In another embodiment of the invention, the means for determining a value correlating with the blood density are provided by a measuring apparatus for determining the hematocrit (HCT) and/or the relative change in hematocrit. If one assumes that during the measuring time, the number of red blood corpuscles and their size remain approximately constant, then the change in hematocrit is inversely proportional to the change in blood volume:

$$RBV(t0)/RBV(t)=HCT(t)/HCT(t0) \quad (5)$$

Using equations (4) and (5), equation (3) can be easily converted into an expression in which, in addition to the pulse transit time measurement, it is then only necessary to indicate the relative change in hematocrit HCT(t)/HCT(t0).

Furthermore, the device according to the present invention exhibits advantageously as part of the evaluation unit an evaluation step that examines the values compensated according to equation (3a) or (3b) for abnormal values, using predefined criteria. For example, simple alarm threshold values can be set absolute or relative. The increase in pulse transit time over time t can also represent an alarm criterion. Lastly, if a calibration has been carried out with an absolute blood pressure measuring device, the pulse transit time can first be converted into an absolute blood pressure value and the alarm criteria can be applied to this value.

A preferred embodiment of the device, according to the invention, contains a unit for providing an EKG. The evaluation unit determines from the EKG the first reference point, ta, of the pulse transit time PTT. In addition, at a point at a distance from the heart, a unit for detecting the pulse waves is provided. The evaluation unit determines from the signal of this system the second reference point, te, of the pulse transit time PTT. In a preferred embodiment the detection unit is a photoplethysmograph. The pulse transit time PTT is shown as the interval between the two reference points (PTT=te-ta).

In a particularly advantageous embodiment, the means for determining the pulse transit time comprise at the same time the means for determining a value correlating with the blood density. Thus, for example, a photoplethysmograph can be used at the same time to determine the hematocrit.

The evaluation unit can also handle input and output functions with respect to the operating personnel as they are sufficiently well-known in the state of the art.

At this point it should be pointed out that the concept of the claimed invention can also be reapplied to the effect that the pulse transit time is not measured, but rather the pulse wave propagation velocity is directly measured. As evident from the equation (2), the dependency of the measurement values on the blood density can also be transferred directly to the pulse wave propagation velocity without diverging from the core idea of the invention. This case is regarded as an equivalent implementation of the invention.

The present invention is also directed to the problem of improving a hemotherapeutic arrangement with an extracorporeal blood circulation and a device for determining the pulse transit time of a patient or donor in such a manner that the changes in the blood count are taken into consideration over time and a more accurate monitoring of the pulse transit time and thereby of the blood pressure is thus made possible.

According to the invention, this problem is solved by a hemotherapeutic arrangement with an extracorporeal blood circulation and having a blood supply line connected at one end to the intake of the hemotherapeutic arrangement and at the other end for connection to the patient's or donor's vascular system, a blood removal line connected at one end to the outlet of the hemotherapeutic arrangement and at the other end for connection to the patient's or donor's vascular system, in which the arrangement has a device for determining the pulse transit time with means for determining the pulse transit time of pulse waves, which are propagated via the patient's or donor's vascular system and are created by heart contractions, means for determining a value correlating with the blood density, and an evaluation unit that compensates for the influence of the blood density on the pulse transit time.

As already stated above, in particular for extracorporeal hemotherapy, a constant observation of values, like the patient's or donor's blood pressure, is helpful. At the same time the blood count is automatically modified during hemotherapy. In particular, in the case of hemodialysis and/or hemofiltration, a change in blood volume also takes place. These forms of treatment, which are intended to replace the functions of the human kidney or at least supplement them, have the purpose, among other things, of controlling a patient's fluid balance. At each treatment, a few liters of fluid are withdrawn from the patient during approximately 4–6 hours of treatment time. Hence there is a considerable change in blood density, even if fluid from other fluid compartments of the body flows in.

Integrating a device, for determining the pulse transmit time, as just summarized, into such a hemotherapeutic arrangement enables a continuous, precise blood pressure measurement. In addition, the actuator and sensor technology of the existing apparatus can be resorted to. As already described in EP-A 0 911 044, the unit for detecting the pulse waves at a point at a distance from the heart can comprise a measuring sensor that is already a part of the hemotherapeutic arrangement.

In an advantageous embodiment of the invention, this is the arterial pressure sensor, i.e., the pressure sensor that is attached to the blood supply line for a hemotherapeutic arrangement.

In the state of the art, there exist other sensors, by means of which blood volume and hematocrit changes can be determined extracorporeally. The EP-A 0 358 873 describes a system for determining the ultrasonic runtime that calculates from ultrasonic runtime the relative change in blood volume and/or hematocrit. There exist optical methods that determine with the optical direct light method the hematocrit concentration at the extracorporeal blood supply line, on the basis of which the hematocrit and relative blood volumes are derived. Such a process is the object of WO 94/27495, for example. A combination of an optical direct light method with a scattered light method, in which only a light wavelength needs to be used is proposed by WO 00/33053.

Other details and advantages of the invention are described in greater detail with reference to the embodiments illustrated in the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
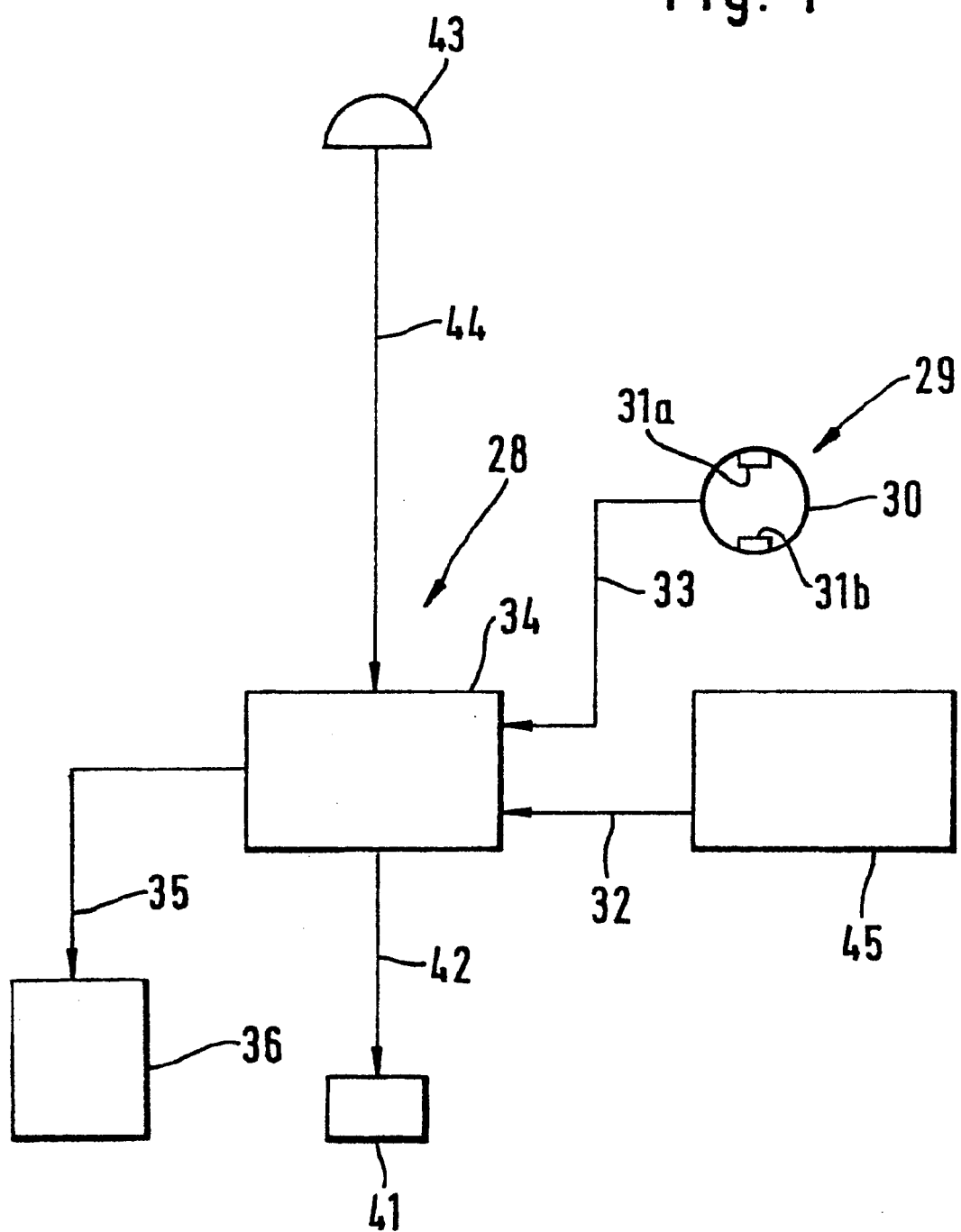
FIG. 1 is a schematic diagram of a device, according to the invention, for applying the inventive process for determining the pulse transit time in the sense of an independent monitor.

The measuring device 28, depicted in FIG. 1, for determining the pulse transit time for a patient or donor, has an electrocardiograph 45, an absolute blood pressure measuring device 43, designed as a pressure cuff, a photoplethysmograph 29 and an evaluation unit 34. All sensor components are connected to the evaluation unit with corresponding lines 32, 33 and 44. The electrocardiograph 45 provides the voltage signals using electrodes (not shown in greater detail). Said signals are generated by means of the heart stimulation (EKG) on the surface of the patient's or donor's body. These signals are made accessible via the line 32 of the evaluation unit 34. It determines from the position of the R peak the first reference point, ta, for determining the pulse transit time.

The photoplethysmograph 29 has a sensor 30 that includes an infrared light source 31a and a light detector 31b. In this embodiment the light source and the light detector are designed in such a manner that three LEDs and three photodiodes make measurements possible in the three wavelengths 805 nm, 970 nm and 1,310 nm. Such a photoplethysmograph is described in WO 94/23643, which is hereby incorporated by reference.

The photoplethysmograph 29 is attached to a part of the body, preferably to a finger or earlobe of the patient or donor in such a manner that the light at least partially penetrates the body part before it hits the photodiodes 31b. This can take place in a direct light arrangement, but in principle also in a scattered light arrangement. The measurement signals are sent via the line 33 to the evaluation unit 34 that comprises means to determine from the curve the second reference point of the pulse transit time. This can take place according to the process mentioned in EP-A 0 911 044. For this, only the measurement with a wavelength is necessary at first. Pulse waves cause an expansion of the vessels in the blood vessels, thus leading to a modified absorption by the modified quantity of blood and thus also the blood constituents. In the described 3-wavelength photoplethysmograph, this applies to all three wavelengths 805 nm, 970 nm and 1,030 nm, whereby the measurements in the first two wavelengths are sensitive to the substances hemoglobin and oxyhemoglobin and whereby the measurement with the third wavelength concerns plasma water absorption.

The absolute blood pressure measuring apparatus 43 can be used to calibrate the pulse transit time measurements. Subsequent pulse transit time measurements can then be converted by the evaluation unit 43 directly into absolute blood pressure data and, if desired, they can be indicated. For greater details see also the EP-A 0 911 044.

For a pulse transit time measurement, compensated for blood density, the measuring device 28 works as follows. At a first time t0, the evaluation unit 34 determines from an incoming EKG signal (first reference point, ta) and a subsequent pulse signal of the photoplethysmograph 29 (second reference point, te) a first pulse transit time PTT (t0,p(t0), ρ(t0)). (Since the PTT values (≈0.15 . . . 0.3a) are small compared to the time periods of consecutive PTT measurements that concern significant changes in blood pressure, it is inconsequential whether for ta, te or a time between these two times is chosen for t0). At the same time, with the help of the photoplethysmograph 29, the hematocrit of the patient's or donor's blood is determined. For this, absorption measurements are carried out for all three of the aforementioned wavelengths and evaluated as described in WO 94/23643. An absolute value for the hematocrit HCT (t0) at time t0 is then obtained.

The initiation of this time t0 can be brought about by an automatically running program or by a signal from outside-manually or via an interface connection. The same applies to the initiation of a second measurement at a time t with t>t0, for which the pulse transit time PTT (t,p(t),ρ(t)) as well as a corresponding value HCT(t) are measured.

Then the means for blood density compensation of the pulse transit time in the evaluation unit 34 calculate the blood density-compensated pulse transit time PTT (t,p(t),ρ(t0)) and, respectively, PTT (t0,p(t0),ρ(t)).

The value obtained can then be indicated directly or after conversion into a blood pressure value, if a calibration was carried out using the absolute blood pressure measuring apparatus 43, on a display unit 36 that is connected to the evaluation unit 34 via a line 35. In addition, alarms 41 can be provided that are connected with a line 42 to the evaluation unit 34. These are suitable for emitting acoustical or optical alarm signals, if the evaluation unit 34 gives a corresponding signal for this. This then occurs when the evaluation unit indicates an abnormal condition using the obtained blood pressure or pulse transit time values, e.g. when the threshold value is exceeded or falls below or when the value changes too quickly within a brief time.

Figure 2:
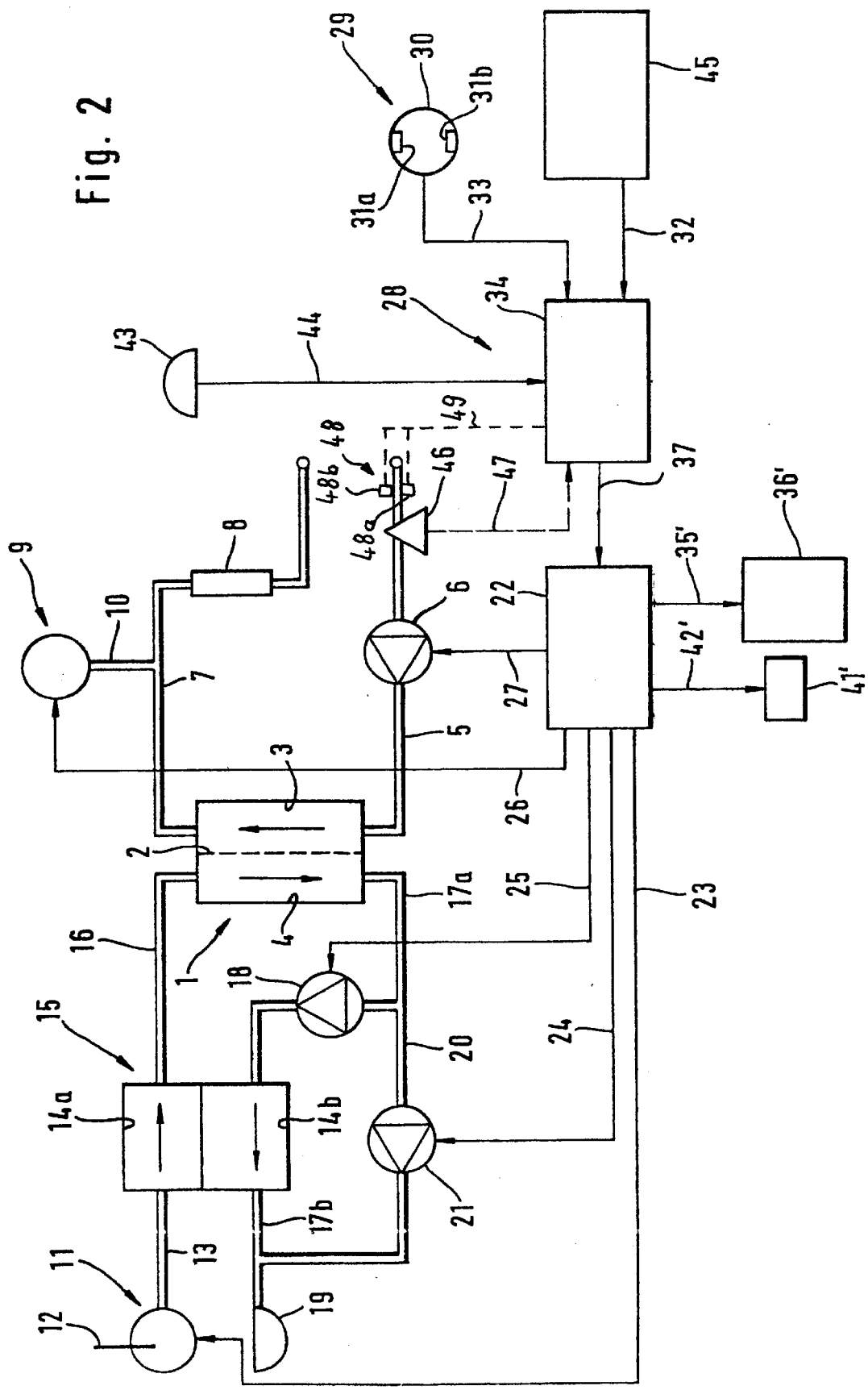
FIG. 2 is a schematic diagram of an extracorporeal hemotherapeutic arrangement, consisting of a hemodialysis unit with a device, according to FIG. 1.

FIG. 2 shows a hemotherapeutic arrangement with a hemodialyzer as the hemotherapy unit. This apparatus corresponds roughly to the device described in EP-A 0 911 044. The essential components are briefly described here nevertheless. The hemotherapeutic arrangement has a hemodialyzer 1 that is separated by a semipermeable membrane 2 into a blood chamber 3 and a dialyzer fluid chamber 4. The intake of the blood chamber is connected to one end of a blood supply line 5, into which a blood pump 6 is connected, while the outlet of the blood chamber 3 is connected to one end of a blood supply line 7, into which a drip chamber 8 is connected. The extracorporeal blood circulation also has a unit 9 for automatic application of an infusion, in particular of a physiological NaCl solution (typically 200 ml) or also online filtered substitute solution at a substitution rate of typically 150 ml/min. The infusion, that usually takes place in bolus-like form, is fed to the patient via a feed line 10 that is connected upstream from the drip chamber 8 to the blood supply line 7.

The dialysis fluid system of the hemodialysis device also comprises a unit 11 for preparation of the dialysis fluid, whereby different compounds of the dialysis fluid (electrolytic administration) can be specified. The dialysis fluid preparation unit 11 has a temperature equalizing unit 12, with which the temperature of the dialysis fluid can be set to various values and kept constant. It is connected via the first section 13 of a dialysis fluid feed line to the inlet of the first chamber half 14a of a balancing unit 15. The second section 16 of the dialysis fluid feed line connects the outlet of the first balancing chamber half 14a to the intake of the dialysis fluid chamber 4. The outlet of the dialysis fluid chamber 4 is connected via the first section 17 of a dialysis fluid removal line to the intake of the second balancing chamber half 14b. A dialysis fluid pump 18 is connected into the first section 17a of the dialysis fluid removal line. The outlet of the second balancing chamber half 14b is connected via the second section 17b of the dialysis fluid removal line to the outlet 19. Upstream from the dialysis fluid pump 18, an ultrafiltrate line 20, also leading to the outlet 19, branches off from the dialysis fluid removal line 17. An ultrafiltration pump 21 is connected into the ultrafiltrate line 20.

The hemodialysis device also comprises a central control unit 22 that is connected via control lines 23 through 27 to the blood pump 6, the dialysis fluid pump 18, the ultrafiltration pump 21, the unit 11 for preparation of the dialysis fluid and the unit 9 for automatic application of a bolus.

During the hemodialysis treatment, the patient's blood flows through the blood chamber 3; and the dialysis fluid flows through the dialysis fluid chamber 4 of the dialyzer 1. Since the balancing unit 15 is connected into the dialysis fluid path, only as much dialyzer fluid can flow through the dialysis fluid supply line 16 as dialysis fluid can flow out through the dialysis fluid removal line 17. Fluid can be removed from the patient with the ultrafiltration pump 21.

The hemodialysis device also has a device 28 for continuous determination of the pulse transit time according to FIG. 1. The reference numerals of these components are the same as in FIG. 1. For practical reasons, the alarm 41 and the display unit 36 are illustrated in the present case by the already present simple elements 41' and 36' together with the control lines 42' and 35' of the hemotherapeutic arrangement, which are connected to the control unit 22. The evaluation unit 34 is also connected via a line 37 to the control unit 22. Both units can indeed represent physically separate units, but they can also be combined in a shared unit, practically the control unit for the hemotherapy device. The separation then has only a functional significance.

The operating mode of the device 28 has already been explained. In the case of the hemodialysis device, according to FIG. 2, the control unit 22 then also receives the blood density-compensated measurement values of the evaluation unit 34. According to the stored alarm criteria, the control unit 22 can propose or, optionally, automatically carry out countermeasures to counteract a recognized critical blood pressure condition.

Owing to the ultrafiltration carried out during the hemodialysis treatment, the patient has considerable quantities of fluid withdrawn, a state that can lead to a decrease in blood pressure (hypotension). By semi-continuous measurement of the blood pressure by means of the pulse transit time method (approximately one measurement per second), a hypotension phase can already be recognized early before noticeable symptoms appear in the patient.

Owing to the evaluation unit 34, these measurement values are then provided with increased accuracy, because the influence of the blood density, changing due to the ultrafiltration, is compensated. A decrease in the relative blood volume by 20% is not rare during hemodialysis. According to equations (3) and (4), the compensation of the blood pressure change results in approximately 20% more precise measurement value for a later measurement of the pulse transit time for a comparison with an earlier measurement.

Examples of countermeasures against a decrease in blood pressure can be introduced by the control unit by a change in the electrolytic concentration through the control line 23, by an initiation of an infusion through the control line 26, by reducing or even switching off the ultrafiltration through the line 24 or even by immediately stopping the treatment by stopping the blood pump 6.

In another embodiment of the invention, an arterial pressure sensor 46 on the blood supply line 5, usually present anyway, is used to detect the second reference point te for the pulse transit time measurement. In this case the pressure sensor 46 is connected via a line 47 to the evaluation unit 34. In this embodiment there is no need for photoplethysmograph 28 for this function.

In a particularly advantageous embodiment the photoplethysmograph 29 can be dispensed with altogether. In this case the means for determining a value correlating with the blood density are provided extracorporeally. To this end, a blood volume monitor 48 can be attached in the manner described in EP-A 0 358 873 to the blood supply line 5. This blood volume monitor consists of an ultrasonic transmitter 48a and an ultrasonic receiver 48b that determine the runtime of the ultrasonic signal through the blood supply line. The blood volume monitor 48 is connected via a line 49 to the evaluation unit 34 that determines from the signals a change in the relative blood volume or the hematocrit between the times t0 and t. It is also conceivable to use other extracorporeal sensors that determine the hematocrit optically or using other measurement variables on the blood supply line, for example.

The handling of functions in the extracorporeal circulation can be divided differently. Thus, for certain situations it may be reasonable to integrate the means for determining a value, correlating with the blood density, into the extracorporeal circulation, but to leave the means for determining the pulse transit time completely directly on the patient's body.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A process for determining the pulse transit time of a patient or donor, in which a pulse transit time is measured for pulse waves, propagating via the patient's or donor's vascular system and created by his/her heart contractions, comprising:
   determining a value, correlating with a blood density; and
   using the value, correlating with the blood density, to calculate, from the pulse transit time measured, a pulse transit time for which an influence of the blood density is compensated.

2. The process, according to claim 1, wherein the value, correlating with the blood density, is one of a relative blood volume or, respectively, a relative change in blood volume.

3. The process, according to claim 1, wherein the value, correlating with the blood density, represents hematocrit or a relative change in hematocrit.

4. The process, according to claim 2, wherein to determine the value, correlating with the blood density, an ultrasonic runtime measurement is carried out on the blood.

5. The process, according to claim 2, wherein to determine the value, correlating with the blood density, an optical direct light measurement and/or scattered light measurement is carried out on the blood.

6. The process, according to claim 1, wherein a pulse transit time PTT (t),p(t),ρ(t0)), compensated with respect to the blood density ρ(t0) at time t0, is determined from a measurement value of the pulse transit time PTT (t,p(t),ρ(t)) for a time t, for the blood density ρ(t) present at this point in time and the present blood pressure p(t), according to the following expression:

$$PTT(t, p(t), \rho(t0)) = PTT(t, p(t), \rho(t))\sqrt{[\rho(t0)/\rho(t)]}.$$

7. The process, according to claim 6, wherein the relation of the blood densities is determined by the expression $$\rho(t0)/\rho(t) = RBV(t)/RBV(t0)$$

with RBV(t0) and RBV(t) representing the corresponding relative blood volumes or, respectively, the quotient representing the relative change in blood volume between the points in time t0 and t.

8. The process, according to claim 6, wherein the relation between the blood densities is expressed by the expression $$\rho(t0)/\rho(t) = HCT(t0)/HCT(t),$$

with HCT(t0) and HCT(t) representing the corresponding hematocrit values or, respectively, the quotient representing the relative change in hematocrit between times t0 and t.

9. A device for determining a patient's or donor's pulse transit time comprising:
   means for determining the pulse transit time of pulse waves, which are propagated via the patient's or donor's vascular system and are created by heart contractions;
   means for determining a value, correlating with blood density; and
   an evaluation unit compensating for an influence of the blood density on the pulse transit time.

10. The device, according to claim 9, wherein the means for determining the pulse transit time comprises a unit to provide an electrocardiogram, and the evaluation unit is suitable to determine a first reference point, ta, of the pulse transit time from the electrocardiogram.

11. The device, according to claim 10, wherein the evaluation unit for the first reference point, ta, determines the time at which the R peak appears on the electrocardiogram.

12. The device, according to claim 10, wherein said means for determining the pulse transit time comprise a unit for detecting the pulse waves at a point at a distance from the heart, the evaluation unit being suitable for determining a second reference point, te, of the pulse transit time from the detection of the pulse waves at a point at a distance from the heart.

13. The device, according to claim 12, wherein the unit for detecting the pulse waves at a point at a distance from the heart is a device for detecting the pulse waves at a point on the body, including a finger of the patient or the donor.

14. The device, according to claim 13, wherein the unit for detecting the pulse waves at a point at a distance from the heart is a photoplethysmograph.

15. The device, according to claim 9, wherein the means for determining a value, correlating with the blood density, comprise a measuring device for determining one of the relative blood volume or, respectively, the relative change in blood volume, such that the relative blood volume or, respectively, the relative change in blood volume represent the value, correlates with the blood density.

16. Device, according to claim 9, wherein the means for determining a value, correlating with the blood density, comprise a measuring device for determining the hematocrit or the relative change in hematocrit, such that the hematocrit or, respectively, the relative change in hematocrit represents the value, correlates with the blood density.

17. The device, according to claim 15, wherein the measuring device is an ultrasonic runtime measuring device.

18. The device, according to claim 15, wherein the measuring device is one of an optical direct light measuring device and a scattered light measuring device.

19. The device, according to claim 9, wherein the evaluation unit determines a pulse transit time PTT (t,p(t),ρ(t0)), compensated with respect to the blood density ρ(t0) at the time t0, from a measurement value of the pulse transit time PTT (t,p(t),ρ(t)) for a time t, for the blood density ρ(t) present at this point in time and the present blood pressure p(t) according to the following expression:

$$PTT(t, p(t), \rho(t0)) = PTT(t, p(t), \rho(t))\sqrt{[\rho(t0)/\rho(t)]}.$$

20. The device, according to claim 19, wherein the relation between the blood densities is represented by the expression $$\rho(t0)/\rho(t) = RBV(t)/RBV(t0)$$

wherein RBV(t0) and RBV(t) represent the corresponding relative blood volumes or, respectively, the quotient represents the relative change in blood volume between the points in time t0 and t.

21. The device, according to claim 19, wherein the relation between the blood densities is represented by the expression $$\rho(t0)/\rho(t) = HCT(t0)/HCT(t),$$

wherein HCT(t0) and HCT(t) represent the corresponding hematocrit values or, respectively, the quotient represents the relative change in hematocrit between times t0 and t.

22. The device, according to claim 9, wherein the device further includes an alarm and the evaluation unit is suitable for recognizing abnormal values of the pulse transit time by means of stored criteria and then setting on the alarm.

23. The device, according to claim 9, wherein the means for determining the pulse transit time comprise the means for determining a value, correlating with the blood density.

24. A hemotherapeutic arrangement with an extracorporeal blood circulation, comprising:
    a hemotherapeutic filter arrangement;
    a blood supply line for connection to a patient or donor, said supply line being connected at one end to an intake of the hemotherapeutic filter arrangement and connectable at the other end to the patient's or donor's vascular system;
    a blood removal line for connection to the patient or donor, said removal line being connected at one end to an outlet of the hemotherapeutic filter arrangement and connectable at the other end to the patient's or donor's vascular system; and
    a device for determining the patient's or donor's pulse transit time including,
        means for determining the pulse transit time of pulse waves, which are propagated via the patient's or donor's vascular system and are created by heart contractions;
        means for determining a value, correlating with blood density; and
        an evaluation unit compensating for an influence of the blood density on the pulse transit time.

25. The hemotherapeutic arrangement according to claim 24, wherein said hemotherapeutic filter arrangement is one of a hemodialyzer and a hemofilter.

26. The hemotherapeutic arrangement according to claim 24, wherein said means for determining the pulse transit time is a unit for detecting the pulse waves at a point at a distance from the heart, said unit including a measuring sensor for detecting a reference point extracorporeally at a point in the extracorporeal blood circulation.

27. The hemotherapeutic arrangement according to claim 26, wherein the measuring sensor is a pressure sensor.

28. The hemotherapeutic arrangement according to claim 24, wherein said means for determining a value, correlating with the blood density, are provided extracorporeally on a point of the extracorporeal blood circulation.

29. The hemotherapeutic arrangement according to claim 28, wherein said means for determining a value includes at least one of an optical direct light sensor and a scattered light sensor.

30. The hemotherapeutic arrangement according to claim 28, wherein said means for determining a value is an ultrasonic runtime sensor.

* * * * *